US008454569B2

(12) United States Patent
Kull-Osterlin et al.

(10) Patent No.: US 8,454,569 B2
(45) Date of Patent: Jun. 4, 2013

(54) CATHETER ASSEMBLY WITH A FOLDED URINE COLLECTION BAG

(75) Inventors: Kristina Kull-Osterlin, Ojersjo (SE); Ian Matthews, Billdal (SE); Peter Risberg, Falkoping (SE)

(73) Assignee: Astra Tech AB, Molndal (SE)

( * ) Notice: Subject to any disclaimer, the term of this patent is extended or adjusted under 35 U.S.C. 154(b) by 629 days.

(21) Appl. No.: 12/337,912

(22) Filed: Dec. 18, 2008

(65) Prior Publication Data

US 2009/0163884 A1  Jun. 25, 2009

Related U.S. Application Data

(60) Provisional application No. 61/008,571, filed on Dec. 21, 2007.

(30) Foreign Application Priority Data

Dec. 21, 2007 (EP) ..................................... 07150341

(51) Int. Cl.
  *A61F 5/44* (2006.01)
(52) U.S. Cl.
  USPC ............ 604/328; 604/331; 604/349; 604/544
(58) Field of Classification Search
  USPC ................. 604/328, 171, 172, 265, 364, 544,
     604/571, 266, 267, 540, 327, 523, 525, 528,
     604/533, 349, 317, 331; 206/363, 364, 370,
     206/438; 53/461
  See application file for complete search history.

(56) References Cited

U.S. PATENT DOCUMENTS

| 2,856,932 | A | | 10/1958 | Griffitts et al. | |
|---|---|---|---|---|---|
| 4,723,944 | A | | 2/1988 | Jensen | |
| 6,004,305 | A | * | 12/1999 | Hursman et al. | 604/328 |
| 6,849,070 | B1 | * | 2/2005 | Hansen et al. | 604/544 |
| 7,066,912 | B2 | * | 6/2006 | Nestenborg et al. | 604/171 |
| 2005/0137582 | A1 | | 6/2005 | Kull-Osterlin et al. | |

FOREIGN PATENT DOCUMENTS

| DE | 20 2006 013 663 U1 | 11/2006 |
|---|---|---|
| EP | 1 634 554 A2 | 3/2006 |
| EP | 1 878 461 A1 | 1/2008 |
| WO | WO-97/26937 A1 | 7/1997 |
| WO | WO-98/11932 A1 | 3/1998 |
| WO | WO-00/16843 A1 | 3/2000 |
| WO | WO-01/43807 A1 | 6/2001 |

* cited by examiner

*Primary Examiner* — Tatyana Zalukaeva
*Assistant Examiner* — Benedict L Hanrahan
(74) *Attorney, Agent, or Firm* — Birch, Stewart, Kolasch & Birch, LLP

(57) ABSTRACT

There is disclosed a catheter assembly comprising a catheter and a receptacle. The receptacle has an elongate pocket, for accommodating at least an insertable end of said catheter, a urine collection bag, having a width extension wider than a greatest width of said elongate pocket, and at least two tab areas on at least one tab are arranged at the periphery of the urine collection bag on opposite sides of said bag. Further, in a storage state, said elongate pocket is folded over said urine collection bag, and lateral parts of said urine collection bag extending outside said elongate pocket are folded towards each other over said elongate pocket, said lateral parts being dimensioned to overlap each other in the folded disposition, and wherein said tab areas are arranged on said lateral parts and are attached to each other, in at least one point of attachment, to releasably maintain said catheter assembly in a folded disposition during storage.

18 Claims, 4 Drawing Sheets

CATHETER ASSEMBLY WITH A FOLDED URINE COLLECTION BAG

TECHNICAL FIELD OF THE INVENTION

The present invention relates to a catheter assembly comprising a catheter and a receptacle, said receptacle having an elongate pocket, for accommodating at least an insertable end of said catheter and a urine collection bag, having a width extension wider than a greatest width of said elongate pocket. The present invention also relates to a method for manufacturing of such a catheter assembly.

BACKGROUND ART

Catheters find their use in many different medical applications, such as urinary catheters for bladder drainage. These urinary catheters are inserted in a variety of populations, including the elderly, stroke victims, spinal cord-injured patients, post-operative patients and those with obstructive uropathy.

In order to maintain the catheter in a clean and preferably sterile condition, each catheter is normally pre-packed in a receptacle by the manufacturer. Furthermore, to facilitate the use and to improve cleanliness of the catheter, the assemblies have in recent years developed to comprise a rupturable wetting fluid pouch or container as well, where wetting of the catheter may be performed without the use of externally supplied water, and without breaking the sealed condition of it until intended use of the catheter. Such assemblies are disclosed in for instance WO 97/26937, WO 01/43807 and WO 98/11932. These documents further describe receptacles accommodating catheters, which receptacles may form urine collection bags. For such assemblies, the receptacle is not ripped off and then disposed off, instead it is maintained connected to the catheter and used as a urine collection bag. Utilizing the receptacle as a container for receiving the drained urine from the bladder may contribute to less spillage, as the catheter maintains connected to the receptacle during, as well as after, the drainage. Naturally, in order to utilize the receptacle as a urine collection bag, the receptacle needs to be of sufficient size.

A larger catheter assembly is however inconvenient, not least for the individuals for whom catheterization is a daily-life procedure. To alleviate the inconvenience, there is a strive for less space consuming catheter assemblies which improve life quality for the user of catheters in that the assemblies can be handled and stored more discreetly, for instance in the pocket of a users clothing. A catheter and a receptacle accommodating the catheter, which receptacle forms a urine collection bag, are thus during storage preferably arranged and maintained in a compact manner, enabling for convenient handling of the assembly prior to use. For instance is the catheter assembly during its manufacturing procedure placed in an enclosing package, in which the assembly is intended to remain until an intended use of the catheter.

Known assemblies of the kind mentioned above, however, require complicated or expensive manufacturing procedures in order to maintain the assembly in a compact and sterile manner during storage, and consequently there is a need for an improved catheter assembly which can be produced more cost-efficiently and is yet compact in the storage stage and convenient to handle in a clean fashion.

SUMMARY OF THE INVENTION

It is therefore an object of the present invention to provide a catheter assembly of the type mentioned by way of introduction and a method for manufacturing the same, in which the above related drawbacks are eliminated wholly or at least partly.

According to a first aspect of the invention, there is provided a catheter assembly comprising a catheter; and a receptacle. The receptacle has: an elongate pocket, for accommodating at least an insertable end of said catheter; a urine collection bag, having a width extension wider than a greatest width of said elongate pocket; and at least two tab areas on at least one tab at the periphery of the urine collection bag on opposite sides of said bag. Further, in a storage state, said elongate pocket is folded over said urine collection bag, and lateral parts of said urine collection bag extending outside said elongate pocket are folded towards each other over said elongate pocket, said lateral parts being dimensioned to overlap each other in the folded disposition, and wherein said tab areas are arranged on said lateral parts and attached to each other, in at least one point of attachment, to releasably maintain said catheter assembly in a folded disposition during storage.

In this context "opposite sides" of said urine collection bag refers to different sides in relation to a central axis through said assembly. Further, "tabs" are in this application used to indicate extensions of the assembly which are not forming part of a compartment wall.

By means of this catheter assembly a very compact product is achieved, having a length that can be as short as half the length of the assembly in the released use state, or even shorter than half the length, and having a width that can be as short as a third of the width of the assembly in the released use state. The width in the storage state can even be shorter than a third of the width in the released state. For example, it is possible to fold the lateral parts more than once, or arrange the lateral parts in a rolled-up arrangement, or the like. Accordingly, the assembly is very convenient to store, and can easily be stowed away in a hand-bag, a hip pocket, or the like. Further, the assembly is very convenient to use, since release of the assembly from the storage state to a unfolded use state is very simple; all that it takes is to release the attachments arranged between the tab areas, and the assembly unfolds. Further, the connection arranged between the tab areas guarantees that the release of the attachment when activating the assembly does not impose any risk of damaging the urine collection bag or the elongate pocket. Thus, the integrity of the inner compartment, and the cleanliness and sterility of the same, can be ensured during the whole process of unfolding the assembly before use. Still further, the new assembly is very cost-effective to produce, since the only additional parts of the assembly required to effect the folded disposition is essentially the provision of the at least one tab, and the connection between the tab areas of said tab. This lowers the material cost of the assembly, and also enables a very cost-efficient production. Accordingly, the provision of envelopes or the like, which is normally required to maintain a product in a folded disposition, can be avoided. The provision of less material in the catheter assembly is also to advantage for the user after the catheterization, since there is less material to be disposed of, making the catheter assembly easier to get rid of in a convenient and non-embarrassing way.

Preferably, the tab areas are attached to each other by means of at least one of welding or gluing. However, other connection alternatives are also feasible, such as Velcro connections and the like.

Further, at least two separated points of attachment are preferably provided, and preferably at least in an upper and lower part of the urine collection bag in relation to the elongate pocket. The lower part of the urine collection bag here refers to the part of the urine collection bag connected to the elongate pocket, and the upper part correspondingly refers to the opposite part of the urine collection bag. Such separate points of attachment may e.g. be provided by provision of two or more pairs of connectable tab areas. This may be accomplished by means of two or more pairs of connectable tabs, or by the provision of one pair of longer tabs, each extending over a substantial part of the periphery of the urine collection bag, or even by the provision of only one tab, extending over a substantial part of the periphery of the urine collection bag.

Preferably, the width extension of the urine collection bag is at least twice the width of said greatest width of the elongate pocket, which will enable an overlap of the lateral parts of the urine collection bag without having to bend or wrinkle the central part there between.

The assembly is particularly useful as a package for housing a hydrophilic urinary catheter, and preferably a catheter intended for intermittent use.

In addition, the assembly preferably comprises a wetting fluid, wherein said wetting fluid in said storage state is kept separated from a hydrophilic surface layer of said catheter, and in an activation state is arranged to be brought into contact with said hydrophilic surface layer prior to an intended use of said catheter. It is further preferred that the wetting fluid is arranged in a sachet which is arranged within the urine collection bag, and, in the storage state, in a central part between said lateral parts. However, even though such an arrangement is preferred, the sachet can in principal be arranged anywhere within the receptacle, and e.g. in one of the lateral parts of the urine collection bag.

A preferred way of ensuring that the release of the connection between the tab areas does not inflict any risk of damage on the urine collection bag, is to arrange a weakening line at least partly encircling the point of attachment in the tab areas, wherein a rupture resulting from releasing said tab areas from one another in said point of attachment, is essentially limited to said weakening line. An alternative way of obtaining essentially the same result is, in at least one of said points of attachment, to provide attachments with a limited maximum holding capacity, such that releasing of said tab areas from one another in said point of attachment results in the attachment breaking, thereby avoiding rupture of the tab(s) or the urine collection bag.

The urine collection bag further preferably comprises a discharge opening for discharge of the urine from said urine collection bag, said discharge opening preferably being formed as a tear line which may be manually torn open when said receptacle is to be opened.

Still further, the elongate pocket preferably has at least one opening for withdrawal of said catheter, through which said insertion end can be propelled and inserted in the urethra of the patient. The non-insertion end of the catheter is preferably provided with an enlarged diameter, and adapted to form a sealed stop against the elongate pocket during withdrawal of the catheter. The elongate pocket may also be provided with at least two separate openings positioned such that an intermediate part of said elongate pocket may be used as an insertion aid for guiding and holding the wetted catheter during insertion into the human cavity, for instance the urethra. Further, the at least one opening provided on the elongate pocket is preferably a tear opening.

The receptacle is preferably formed of two layers of film of a flexible plastics material. The material is in addition at least partly transparent.

According to a second aspect of the invention, there is provided a method of packaging a catheter assembly comprising a catheter and a receptacle, said receptacle having an elongate pocket and a urine collection bag, and said urine collection bag having a width extension wider than a greatest width of said elongate pocket and at least two tab areas arranged on at least one tab at the periphery of the urine collection bag on opposite sides of said bag, said method comprising: accommodating at least an insertable end of said catheter in said elongate pocket; folding said elongate pocket over said urine collection bag; folding the lateral parts of said urine collection bag extending outside said elongate pocket towards each other over said elongate pocket, said lateral parts being dimensioned to overlap each other in the folded disposition; and attaching said tab areas to each other, in at least one point of attachment, to releasably maintain said catheter assembly in a folded disposition during storage.

In accordance with this aspect, similar advantages are obtainable as discussed above in relation to the first aspect.

Other aspects, benefits and advantageous features of the invention will be apparent from the following description and claims.

BRIEF DESCRIPTION OF THE DRAWINGS

The invention will be more apparent from the accompanying drawings, which are provided by way of non-limiting examples.

DETAILED DESCRIPTION OF PREFERRED EMBODIMENTS OF THE INVENTION

Figure 1:
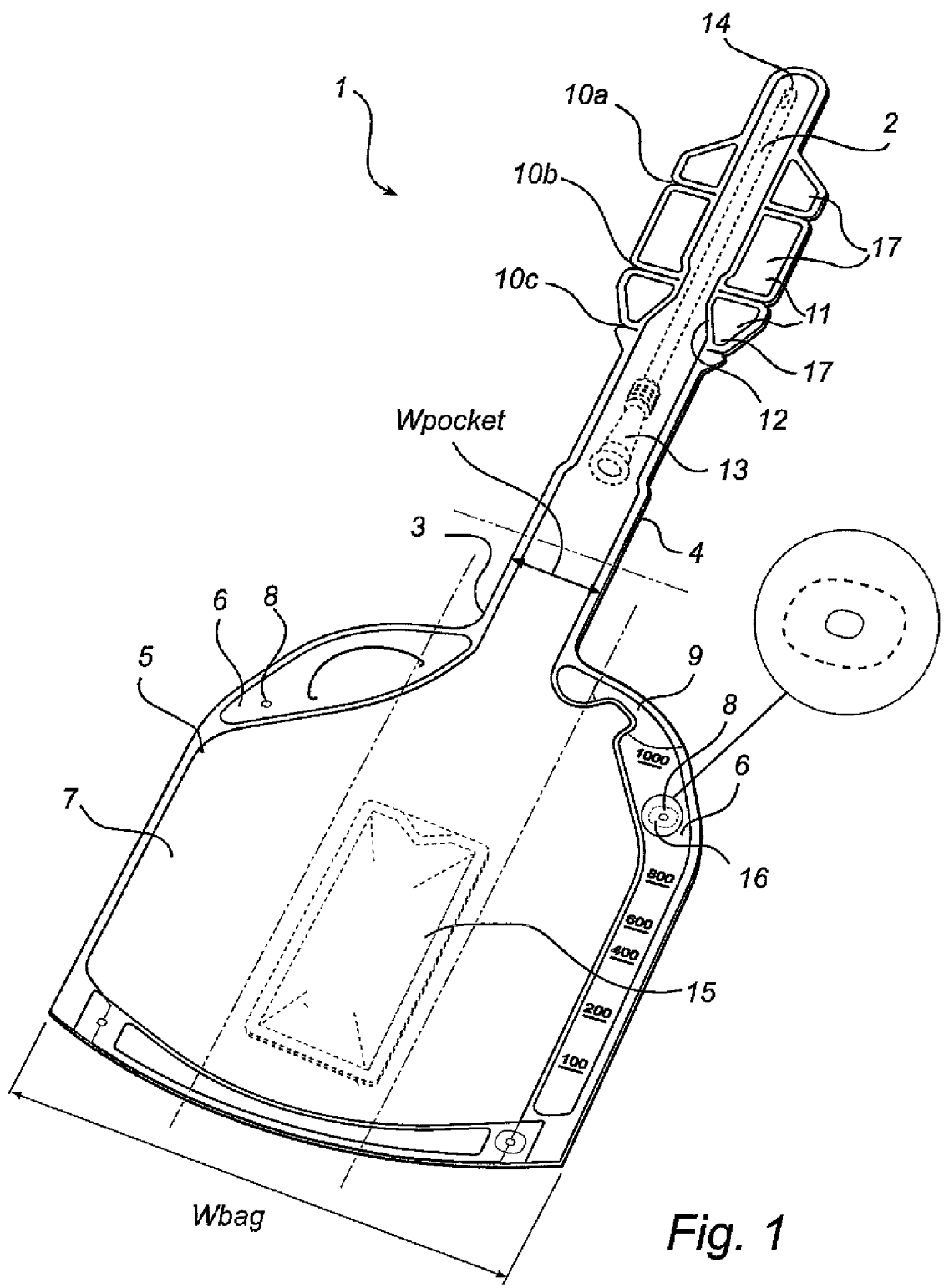
FIG. 1 shows a catheter assembly in an unfolded disposition in accordance with an embodiment of the present invention.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, for instance the length of the catheter, the dimensions of the fluid compartments etc.

FIG. 1 illustrates a catheter assembly 1 in an unfolded disposition according to an embodiment of the present invention.

The catheter assembly 1 comprises a catheter 2, which preferably, although not necessarily, is a hydrophilic urinary catheter and preferably intended for intermittent use. The catheter 2 comprises an elongate shaft having an insertion end 14 and a flared opposite end 13, which flared opposite end 13 may function as a connector of the catheter 2, connectable to other devices such as a urine collection bag, a drainage tube or the like. In the example of FIG. 1, the flared end 13 is a connector 13. An open-ended internal lumen, through which urine is guided during use of the catheter 2, extends from a rounded tip on the insertion end 14 to the flared end 13 of the catheter 2.

At least part of the catheter 2, extending from the insertion end, forms an insertable length to be inserted through a body opening of the user, such as the urethra in case of a urinary catheter 2. By "insertable length" is normally, in the context of a hydrophilic catheter, meant the length of the catheter 2 which is coated with a hydrophilic material, for example PVP, and which is insertable into the urethra of the patient. Typically, this will be 80-140 mm for a female patient and 200-350 mm for a male patient.

According to the invention, and applicable for the embodiments disclosed herein, many different types of well-known hydrophilic surfaces can be used. For example, the catheter 2 may be provided with a hydrophilic coating wherein the hydrophilic polymer coating comprises material selected from polyvinyl compounds, polysaccharides, polyurethanes, polyacrylates or copolymers of vinyl compounds and acrylates or anhydrides, especially polyethyleneoxide, polyvinylpyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

The assembly further comprises a receptacle 3, which has an elongate pocket 4 accommodating the catheter 2. Although the elongate pocket shown in FIG. 1 accommodates the entire catheter 2, the invention is however not restricted thereto; the elongate pocket 4 may likewise accommodate just the insertable part of the catheter 2, or even just a forward part of said insertable part. The receptacle 3 is preferably formed of two layers of film of a transparent flexible plastics material, although other arrangements are possible.

The receptacle 3 comprises a urine collection bag 5, which has a width extension $W_{bag}$ that is wider than a width $W_{pocket}$ of the elongate pocket 4.

Figure 4:
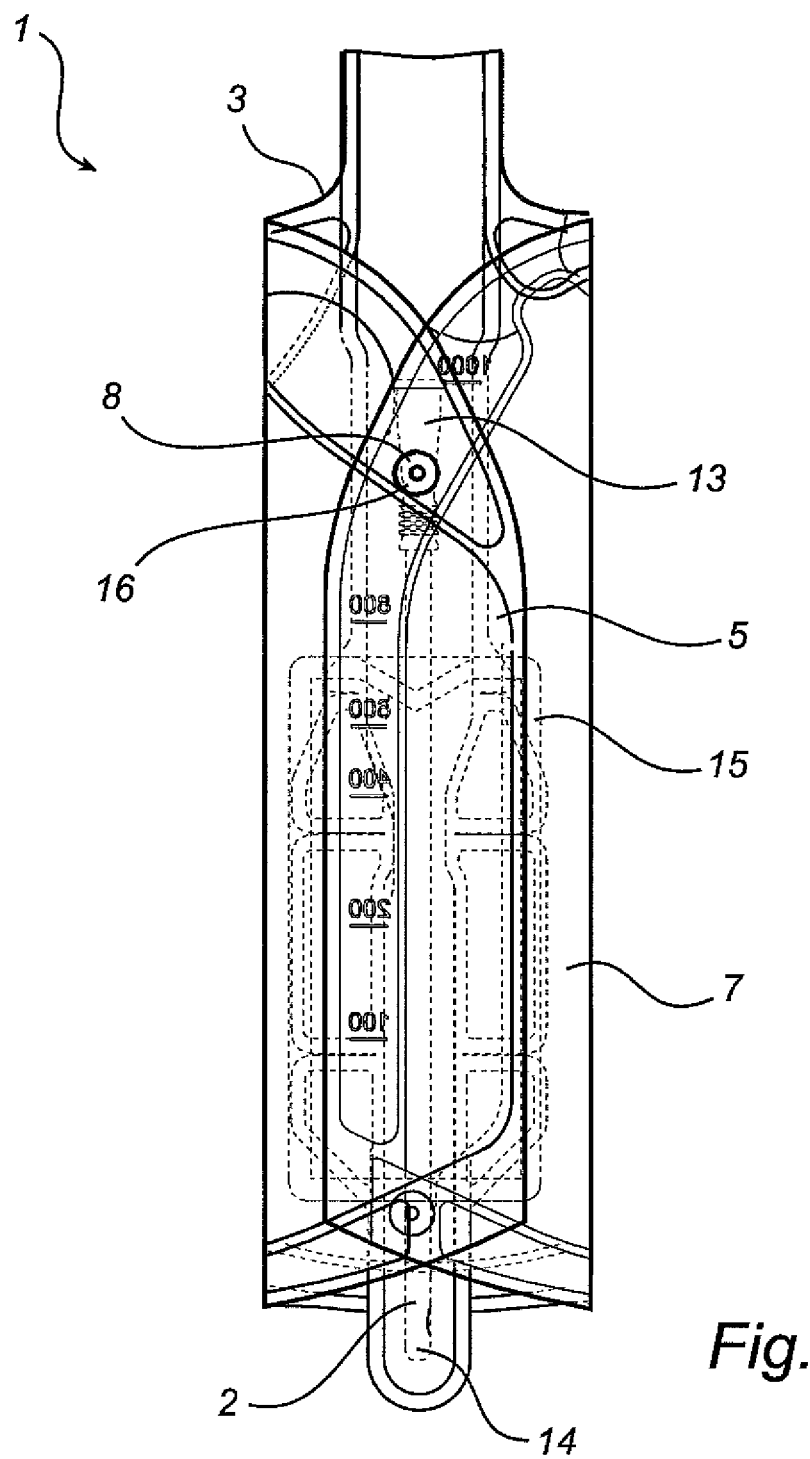
FIG. 4 shows the catheter assembly of FIG. 1 in a folded disposition, with the tab areas at the periphery of the urine collection bag on opposite sides of the bag attached to each other.

Further, the receptacle 3 comprises tab areas on tabs 6 on opposite sides of the urine collection bag 5. The tabs 6 are restricted to being arranged at the periphery of the bag 5, in order not to interfere with a hollow body or compartment 7 of the bag 5. Arranged on the tabs 6 are points of attachment 8, for connecting pairs of tab areas and/or tabs together, and thereby to releasably maintain the catheter assembly 1 in a folded disposition during storage. The folded disposition of the assembly 1 of FIG. 1 is illustrated in FIG. 4. Attachment may for instance be accomplished by means of welding or gluing, or a combination thereof.

Preferably, there are at least two points of attachment 8 on the tabs 6, separated from one another. For each point of attachment 8 in the example, one of the tabs 6 preferably comprises an area 16 encircling the attachment 8, defined by a weakening line. Thus, it is ensured that a rupture resulting from releasing the tabs 6 from one another in that point of attachment 8, is limited to the encircling area 16. The invention is however not restricted to this type of weakening area 16 for avoiding rupture to the urine collection bag 5 as the assembly 1 is released from its folded disposition. A point of attachment 8 may, for instance, likewise comprise a glued or perhaps welded weak attachment, such that when releasing the tabs 6 from one another in that specific point of attachment 8, the attachment 8 gives in, whereby rupture of the urine bag 5 is avoided.

To enable discharge of urine after use of the assembly 1, the urine bag 5 further comprises a discharge opening 9. Preferably, and as illustrated in FIG. 1, the discharge opening 9 is formed as a tear line which may be manually torn open when the receptacle 3 is to be opened.

Prior to an intended use of the catheter 2, an end portion of the elongate pocket must be removed from the catheter assembly 1, or the elongate pocket be opened in any other way, in order to enable withdrawal of at least the insertable part of the catheter 2. Consequently, the receptacle 3 of FIG. 1 preferably comprises opening means 10 for facilitating opening of the receptacle. The opening means 10 may, as shown in FIG. 1, comprise a tear line 10 connected to a gripping handle 17, such as a pulling tab, forming a tear opening. Hereby, the user may pull the gripping handle 17 and, thereby, tearing open the sidewall of the receptacle 3. However, alternative opening means 10 are also feasible, such as tear-lines arranged in different fashions and locations, peel-off joints, etc.

In the example, a plurality of tear openings 10 are arranged on the elongate pocket 4. The type, the number, as well as the positioning of the openings 10 on the receptacle 3 are, however, not limited by the invention.

The elongate pocket 4 of FIG. 1 further comprises a restriction 12, preferably positioned between the end of the elongate pocket 4 housing the insertion end 14 of the catheter 2, and the part of the elongate pocket 4 housing the connector 13. During withdrawal of the catheter 2 from the receptacle 3, the connector 13 then forms a mechanical seal connection with the restriction 12.

Should a user prefer not to use the urine collection bag 5 for collection of urine during use of the catheter 2, the opening 10c placed beneath the restriction 12, is preferably used to remove the urine collection bag 5 along with part of the elongate pocket 3, from the catheter assembly 1. If the user on the other hand chooses to utilize the urine collection bag 5 during drainage, opening 10a and/or 10b are preferably used for withdrawal of the catheter 2.

In FIG. 1, the openings 10 are positioned such that an intermediate part 11 of the elongate pocket 4 may be used as an insertion aid for guiding and holding the wetted catheter 2 during insertion into a human cavity, for instance the urethra.

Upon use, the catheter 2 should be wetted by a wetting fluid. The wetting fluid serves the primary purpose of wetting the hydrophilic surface coating, whereby a low-friction character of the surface is produced and the catheter 2 becomes slippery and easy to insert into, for instance, the urethra of the patient. However, it is also possible to provide a dissolved antimicrobial compound in the fluid. The wetting fluid is preferably a water-based liquid, that is, using water as a solvent. Still further, the wetting fluid could also comprise a dissolved osmolality increasing compound, such as NaCl or the like. Still further, the wetting fluid may comprise a hydrophilic polymer as in the hydrophilic coating of the catheter for which the wetting fluid is intended.

Preferably, the assembly 1 subsequently comprises a wetting fluid forming part of the assembly 1. In the example of FIG. 1, the catheter assembly 1 comprises a wetting fluid pouch 15, in which the wetting fluid is kept separated from the hydrophilic surface of the catheter 2 during storage. The pouch 15 is preferably arranged within the hollow body 7 of the urine collection bag 5, and preferably in the central part of the urine collection bag (see below).

Further, the wetting fluid pouch 15 is openable in order to enable activation of the catheter assembly 1. Activation is performed by opening the pouch 15 and releasing the wetting fluid into the receptacle 3 so that it comes into contact with the hydrophilic coating of the catheter 2. The wetting fluid pouch 15 may be openable by means of pressing, tearing, piercing, breaking or twisting, etc., which is per se well known in the art.

The receptacle 3 preferably forms a sealed compartment around the catheter 2 and at least part of the wetting fluid pouch 15.

Although preferred, the invention is not restricted to the pouch 15 described in the example of FIG. 1. Alternatively, the catheter assembly 110 may comprise a package with several separate compartments, one housing the catheter and one housing the wetting fluids is also disclosed in WO 03/092779, hereby incorporated by reference.

It is likewise possible to arrange the wetting fluid pouch 15 not in a separate compartment of the receptacle 3, but integrated with the compartment holding the catheter 2. Hereby, the catheter 2 is activated already during production, and is then maintained in an activated, ready-to-use condition. Thus, in this embodiment, the hydrophilic surface layer is preserved in a wetted state during accommodation in the receptacle 3 and a ready-to-use catheter 2 is provided. In order to preserve this wetted condition, the compartment formed by the receptacle 3 and the catheter 2 is preferably gas sealed, and further, the receptacle 3 is preferably gas impermeable. In use, the receptacle 3 is simply opened, and the catheter 1 could immediately be introduced into the patient. Such an assembly 1 is for instance disclosed in WO 00/47494, hereby incorporated by reference.

Figure 2:
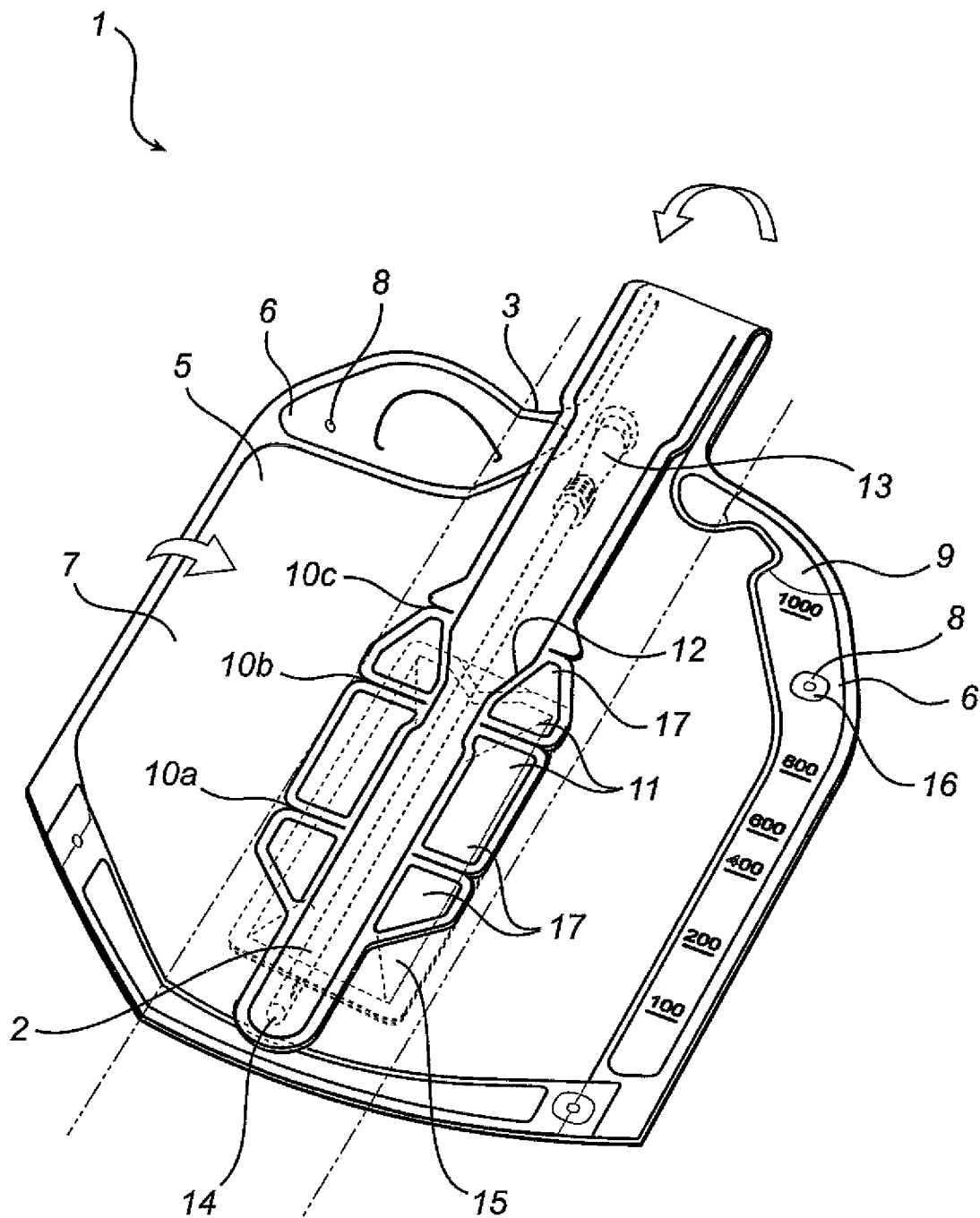
FIG. 2 shows the catheter assembly of FIG. 1, with the elongate pocket folded over the urine collection bag.
Figure 3:
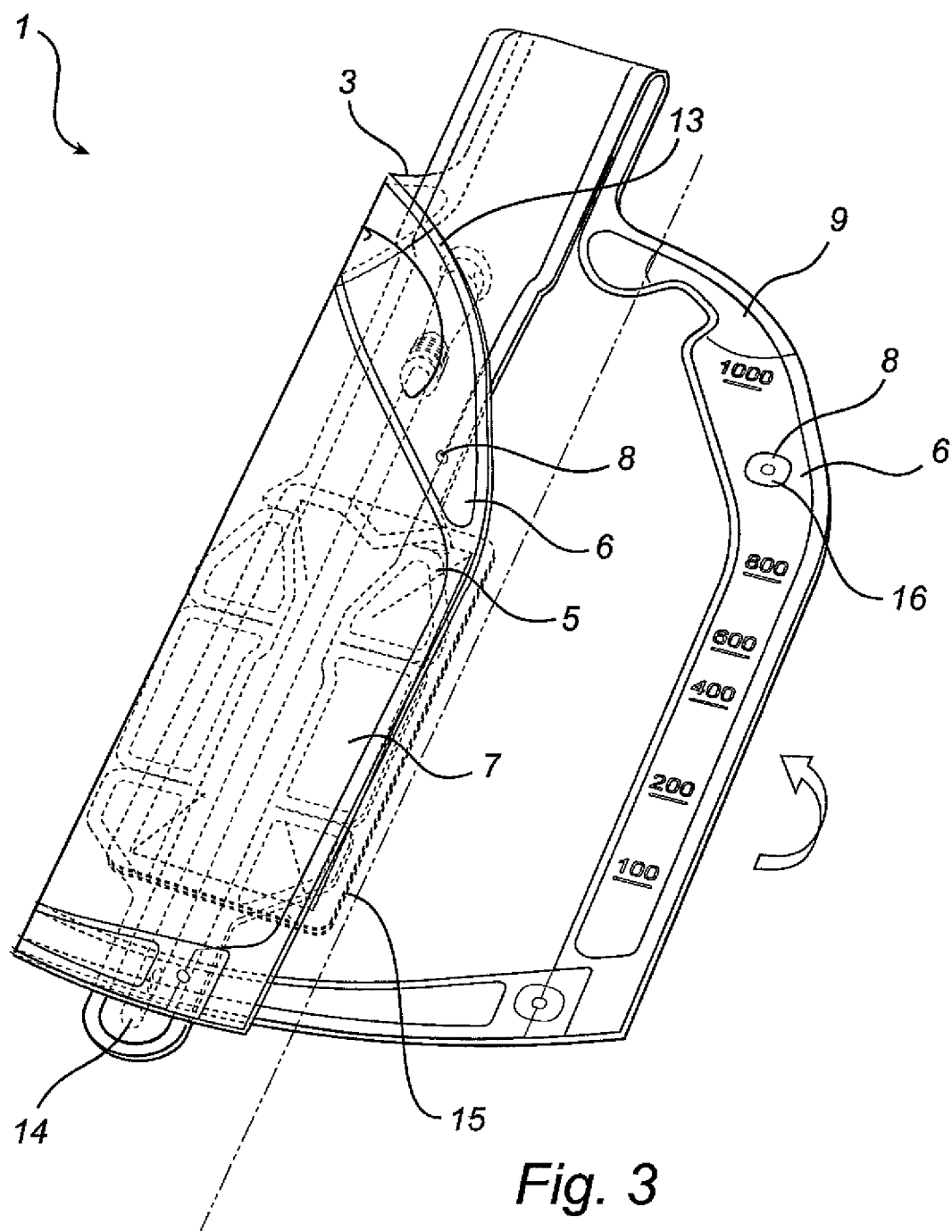
FIG. 3 shows the catheter assembly of FIG. 1, with one of the lateral parts of the urine collection bag folded over the elongate pocket.

In a storage state, the catheter assembly is maintained in a folded disposition. In an exemplifying method of packaging the catheter assembly 1 according to the example of FIG. 1, the catheter 2 is first placed in the elongate pocket 4 of the receptacle 3. Then, the elongate pocket 4 is folded over the urine collection bag 5, resulting in a disposition of the assembly 1 as illustrated in FIG. 2. In the following, the two lateral parts of the urine collection bag 5 are folded towards each other as illustrated by FIG. 3, whereby the assembly 1 assumes the form of a folded disposition as shown in FIG. 4. In order for the assembly 1 to maintain in the folded disposition during storage, the tab areas of the tabs 6 are releasably attached to each other in the provided points of attachment 8.

Reversely, in an exemplifying method of using the catheter assembly 1, the user needs to release the assembly 1 from its folded disposition prior to an intended use. To start with, the two lateral parts of the urine collection bag 5 are carefully pulled apart, whereby the tabs 6 become undone in the points of attachment 8, enabling unfolding of the lateral parts of the bag 5. Then, the elongate pocket 4 is unfolded, and assembly 1 thereby assuming its fully unfolded disposition. Following the unfolding of the assembly 1, the user then activates the surface coating of the catheter 1 by opening the wetting fluid pouch 15 within the bounds of the receptacle 3, thereby releasing the wetting fluid from the pouch 15 into the receptacle 3. After a sufficient wetting period, the receptacle 3 is opened, in order to expose the catheter 2 for insertion into a patient.

In case the user chooses to utilize the receptacle 3 to also serve as a urine collection bag 5, after wetting of the catheter 2 for the predetermined duration, the bag 5 is turned upside down and the elongate pocket 4 end housing the insertion end 14 is torn off. The shaft of the catheter is then maneuvered through the opening in the receptacle 3 and pulled out until the flared end 13 forms a mechanical seal connection with the opening at restriction 12 of the receptacle 3. Thereafter, the catheter 2 is inserted into the urethra of the patient. Thus, being opened, the receptacle 3 maintains connected to the catheter 2 for receiving the drained urine from the bladder. However, this is merely optional, and the user may likewise choose to dispose the urine collection bag 5 prior to use, as described above. The invention has now been discussed in relation to different embodiments. However, it should be appreciated by those skilled in the art that several further alternatives are possible. For example, the features of the different embodiments discussed above may naturally be combined in many other ways.

It is further possible to use the invention for other types of catheters 2 than urinary catheters, such as vascular catheters or the like.

Still further, it is possible to arrange the wetting fluid pouch 15 in many different ways. For example, the pouch may be a separate pouch, but forming part of the assembly 1. Such a wetting fluid pouch 15 may be arranged completely inside the receptacle 3, partly inside the receptacle 3, or completely outside the receptacle 3. Alternatively, the wetting fluid pouch 15 may be an integrated compartment of the receptacle 3. This compartment may be separated from the compartment housing the insertable part of the catheter 1, or be integrated with such a compartment. In the latter case, the catheter 2 may be maintained in a wetted, activated state.

Further, the wetting fluid pouch 15 may be arranged close to the insertion end 14 of the catheter, close to the flared opposite end 13 of the catheter 2, or in any other suitable location in the assembly 1. In case the wetting fluid is arranged separately from the insertable part of the catheter 2, the separation wall or joint could e.g. be a breakable or peelable membrane wall, but alternative embodiments are naturally feasible, such as various types of detachable or openable caps or closings. The wetting fluid pouch 15 may be arranged to be discharged upon application of a twist, a compression, a pull or the like on the fluid pouch 15. Preferably the wetting fluid may be discharged without breaking or rupturing the receptacle 3, even though this may not be necessary, depending on the intended use, etc.

Many different materials could also be used for the different parts of the catheter assembly 1.

It will be appreciated by those skilled in the art that several such alternatives similar to those described above could be used without departing from the spirit of the invention, and all such modifications should be regarded as a part of the present invention, as defined in the appended claims.

The invention claimed is:

1. A catheter assembly comprising
a catheter; and
a receptacle, said receptacle having:
an elongate pocket, for accommodating at least an insertable end of said catheter;
a urine collection bag, having a width extension wider than a greatest width of said elongate pocket; and
at least two tab areas are arranged at the periphery of the urine collection bag on opposite sides of said bag;
at least two attaching members arranged separately on an upper and lower part of the receptacle, each attaching member including a first part and a second part, said first part and second part being arranged on the at least two tab areas, respectively,
wherein said catheter assembly is configurable between a storage state prior to use and a use state,
wherein, in the storage state, said elongate pocket is configured to be foldable over said urine collection bag at a folding position of the elongate pocket where the catheter is not present, and lateral parts of said urine collection bag extending outside said elongate pocket are configured to be foldable towards each other over said elongate pocket, said lateral parts being dimensioned to overlap each other in the folded disposition, and wherein said tab areas are arranged on said lateral parts and are attached to each other by engaging the first parts and second parts of the at least two attaching members, to releasably maintain said catheter assembly in a folded disposition during storage, and wherein in the use state, said catheter assembly is unfolded.

2. The catheter assembly in accordance with claim 1, wherein said tab areas are attached to each other by means of at least one of welding or gluing.

3. The catheter assembly in accordance with claim 1, wherein the width extension of the urine collection bag is at least twice the width of the greatest width of the elongate pocket.

4. The catheter assembly in accordance with claim 1, wherein said catheter is a hydrophilic urinary catheter, and preferably intended for intermittent use.

5. The catheter assembly in accordance with claim 4, further comprising a wetting fluid, wherein said wetting fluid in said storage state is kept separated from a hydrophilic surface layer of said catheter, and in an activation state is arranged to be brought into contact with said hydrophilic surface layer prior to an intended use of said catheter.

6. The catheter assembly in accordance with claim 5, wherein the wetting fluid is arranged in a pouch or sachet which is arranged within the urine collection bag, and, in the storage state, in a central part between said lateral parts.

7. The catheter assembly in accordance with claim 1, wherein at least one of said tab areas for said at least two attaching members comprises weakening lines at least partly encircling said at least two attaching members, wherein a rupture resulting from releasing said tab areas from one another in said at least two attaching members, is essentially limited to said weakening lines.

8. The catheter assembly in accordance with claim 1, wherein at least two attaching members have a limited maximum holding capacity, such that releasing of said tab areas from one another results in the attachment breaking, thereby avoiding rupture of the tab(s) or the urine collection bag.

9. The catheter assembly in accordance with claim 1, wherein said urine collection bag comprises a discharge opening for discharge of the urine from said urine collection bag, said discharge opening preferably being formed as a tear line which may be manually torn open when said urine collection bag is to be opened.

10. The catheter assembly in accordance claim 1, wherein said elongate pocket has at least one opening for withdrawal of said catheter.

11. The catheter assembly in accordance with claim 10, wherein said elongate pocket has at least two separate openings positioned such that an intermediate part of said elongate pocket may be used as an insertion aid for guiding and holding the wetted catheter during insertion into the human cavity, for instance the urethra.

12. The catheter assembly in accordance with claim 10, wherein said at least one opening is a tear opening.

13. The catheter assembly in accordance with claim 1, wherein said receptacle is formed of two layers of film of a flexible plastics material.

14. The catheter assembly in accordance with claim 2, wherein the width extension of the urine collection bag is at least twice the width of the greatest width of the elongate pocket.

15. The catheter assembly in accordance with claim 1, wherein the width extension of the urine collection bag is at least twice the width of the greatest width of the elongate pocket.

16. The catheter assembly in accordance with claim 2, wherein said catheter is a hydrophilic urinary catheter, and preferably intended for intermittent use.

17. The catheter assembly in accordance with claim 1, wherein said catheter is a hydrophilic urinary catheter, and preferably intended for intermittent use.

18. The catheter assembly in accordance with claim 1, wherein the catheter has a flared end, the elongated pocket includes a restriction portion where a width of the elongated pocket decreases, and the restriction portion is configured to be engageable with the flared end of the catheter to form a mechanical seal, so that the receptacle maintains connected to the catheter during the use the catheter.

* * * * *